United States Patent

(12) United States Patent
Grane et al.

(10) Patent No.: US 7,464,601 B2
(45) Date of Patent: Dec. 16, 2008

(54) DISPOSABLE MANOMETER FOR USE WITH PATIENT BREATHING SYSTEMS

(75) Inventors: Christian Grane, Kokkedal (DK); Jakob Bonnelykke Kristensen, Olstykke (DK)

(73) Assignee: Ambu International A/S, Ballerup (DK)

( * ) Notice: Subject to any disclaimer, the term of this patent is extended or adjusted under 35 U.S.C. 154(b) by 210 days.

(21) Appl. No.: 11/477,808

(22) Filed: Jun. 30, 2006

(65) Prior Publication Data

US 2008/0004541 A1    Jan. 3, 2008

(51) Int. Cl.
*G01L 13/02* (2006.01)
(52) U.S. Cl. ......................................... 73/716; 600/486
(58) Field of Classification Search ................... 73/736, 73/716, 715; 600/486, 532
See application file for complete search history.

(56) References Cited

U.S. PATENT DOCUMENTS

| | | | | |
|---|---|---|---|---|
| 3,890,842 A | * | 6/1975 | Ramsey, III | 73/731 |
| 3,890,962 A | * | 6/1975 | Ramsey, III | 600/486 |
| 5,140,982 A | | 8/1992 | Bauman | |
| 5,537,998 A | | 7/1996 | Bauman | |
| 5,557,049 A | * | 9/1996 | Ratner | 73/715 |
| 5,606,131 A | | 2/1997 | Pope | |
| 6,820,620 B2 | | 11/2004 | Rochat | |
| 6,854,334 B2 | | 2/2005 | Ratner | |
| 6,886,561 B2 | | 5/2005 | Bayron et al. | |
| 6,892,728 B2 | | 5/2005 | Helgesson et al. | |
| 7,051,596 B1 | * | 5/2006 | Lau et al. | 73/716 |
| 7,357,033 B2 | * | 4/2008 | Lau et al. | 73/736 |

FOREIGN PATENT DOCUMENTS

SU        1744477 A  *  6/1992

* cited by examiner

*Primary Examiner*—Andre J Allen
(74) *Attorney, Agent, or Firm*—Levy & Grandinetti

(57) ABSTRACT

A disposable manometer for use with a breathing system for monitoring a patient during positive pressure ventilation. The disposable manometer includes a housing with an upper and lower portion, a moving member and a flexible rolling diaphragm sealing mechanism between the moving member and the upper portion of the housing. A calibrated tension means resists movement of the moving member and provides accurate measurement of the ventilation pressure.

11 Claims, 3 Drawing Sheets

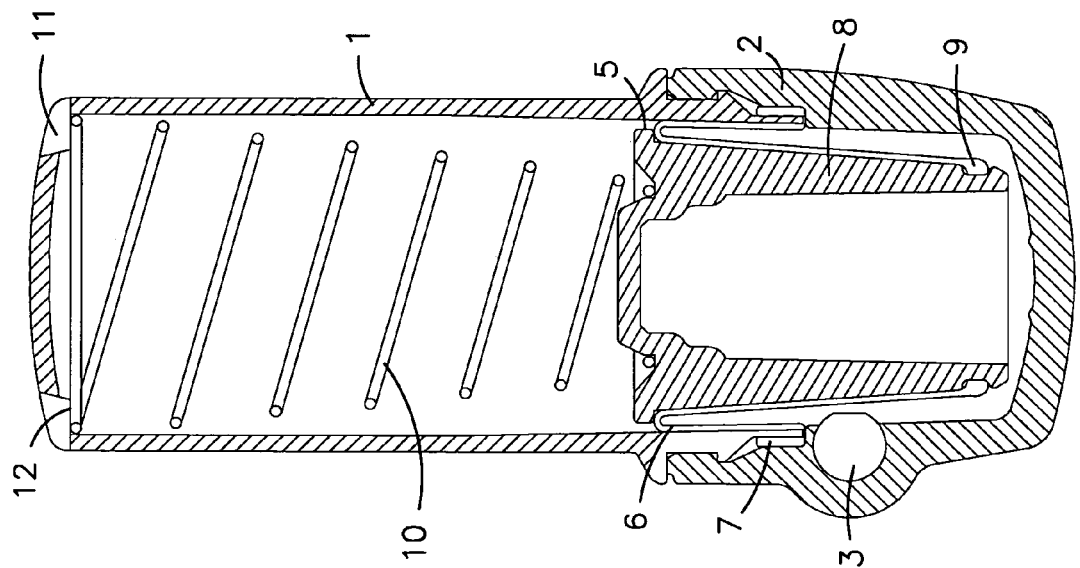
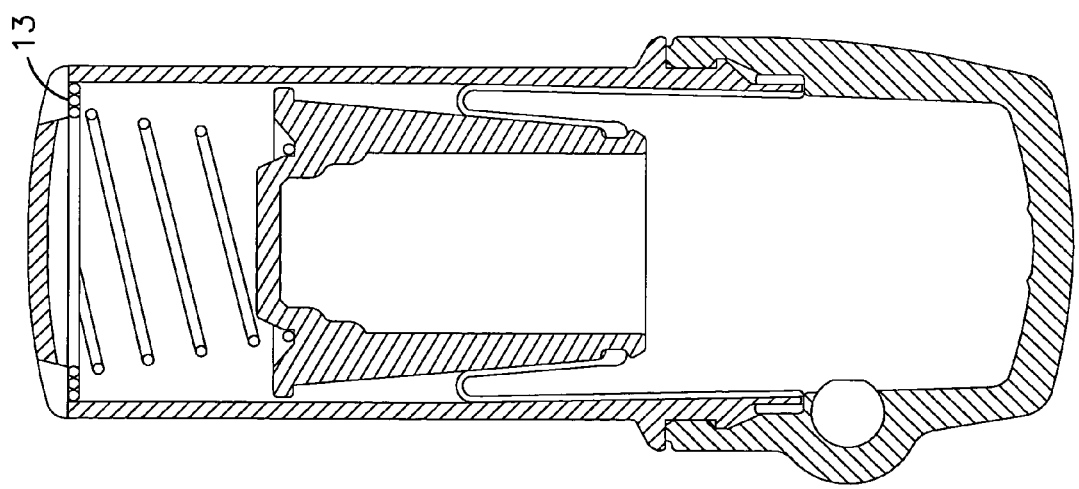

DISPOSABLE MANOMETER FOR USE WITH PATIENT BREATHING SYSTEMS

BACKGROUND OF THE INVENTION

1. Field of the Invention

The invention relates to a manometer for measuring positive pressure of breathing gases in breathing systems during positive pressure ventilation of patients. More particularly, the present invention relates to a low cost and low weight disposable manometer with a non-linear pressure range that provides the operator with adequate accuracy of the relevant breathing gas pressure, while minimizing the overall length of the manometer for ease of handling with the breathing system.

2. Description of Related Art

It is common practice to connect a manometer to a breathing system for monitoring the pressure near the connection of the breathing system to the patient. Often this procedure is performed by connecting a reusable stationary manometer via a small-bore flexible hose to a monitoring port on the breathing system. However, the use of such a reusable attachment to the breathing system does include a risk of transmission of infectious diseases. This procedure is also inconvenient during the transport of a patient as well as during ventilation of a patient in a location where stationary manometers are not readily available. In recent years, there have been efforts to develop disposable manometers suitable for direct connection to disposable, portable breathing systems, such as manually operated resuscitators and hyperinflation bags.

U.S. Pat. No. 5,140,982 to Bauman discloses a resuscitator. The resuscitator includes a ventilation mask for sealing and surrounding a patient's mouth and nose, a gas flow manifold having a passage for delivering ventilating gas to the mask, and a manually collapsible gas receptacle coupled to the gas flow manifold. The resuscitator includes a modular structure for detecting gas pressure in the manifold. The modular structure includes a port communicating with the gas flow manifold to communicate gas pressure in the manifold to a bore. A plunger is mounted to the bore, and a transparent wall structure permits the observation of movement of the plunger wherein the transparent wall has indicia to indicate the pressure detected by the plunger.

U.S. Pat. No. 5,537,998 to Bauman discloses an emergency manual resuscitator with means for detecting air pressure. The resuscitator includes a elastomeric bag connected to a resuscitator assembly. The resuscitator also includes a one-way flap valve. The bag, when compressed manually, causes air to flow to the resuscitator assembly. The bag, when allowed to expand, causes air to flow into the bag past the one-way flap valve. A hollow plunger is movable when the bag is compressed. An air pressure release hole in the cylinder releases excess air pressure in the cylinder to the exterior only after the plunger has been moved by air pressure.

U.S. Pat. No. 5,557,049 to Ratner discloses a disposable manometer for use with a CPR bag. The manometer includes a chamber connected to a source of CPR air pressure via a patient breathing valve and an elongated restricted passageway. The manometer includes a dial and a pointer to indicate the pressure sensed within a manometer chamber. The pointer has an actuator stem at the center of a diaphragm forming one wall of the manometer chamber. The diaphragm is responsive to pressurized air entering the manometer chamber. The diaphragm reciprocates against the force of a biasing spring moving the pointer to indicate the pressure within the manometer chamber. The disposable manometer is intended to be used with a CPR bag or a patient breathing tube.

U.S. Pat. No. 5,606,131 to Pope discloses a piston manometer with spring constant dependent upon position. The manometer is used in a patient's breathing circuit and includes a housing forming a bore and a "slider" within the bore. The slider is movable between an at-rest position, an expanded pressure range, and a contracted pressure range. A spring is connected to the slider for urging the slider toward the at-rest position, while allowing movement of the slider in the two ranges due to the pressure in the breathing circuit. The housing is connected to the breathing circuit such that the gas pressure moves the slider from the at-rest position and into at least the expanded pressure range. At relatively low pressures the slider is moved into the expanded pressure range, and at higher pressures the slider is moved into the contracted pressure range against the force of the spring. The spring is formed by a relatively short tension spring and a relatively long tension spring.

U.S. Pat. No. 6,854,334 to Ratner discloses a negative inspiratory force manometer apparatus. The apparatus is connected by tubing to a patient. The apparatus has a manometer on one side in communication with an entrance port conveying ambient air to the patient. A spring loaded cap is depressed to block air inspired by the patient and to cause such air to move a diaphragm in the manometer so that the inspired negative air pressure of the patient can be recorded. As soon as the cap is released, a spring opens the entrance port to continue normal flow of ambient air to the patient.

It is common practice in medicine to measure the pressure of a patient's breathing with a reusable stationary manometer attached to a breathing system with a flexible hose. The use of a reusable manometer presents the risk of transmitting infectious diseases. Furthermore, the use of current reusable stationary manometers is inconvenient during patient transport and in locations where stationary manometers are not available. The medical industry lacks a disposable, economical manometer that solves these problems and that is compact and easily operated.

SUMMARY OF THE INVENTION

The present invention is directed to a disposable manometer for use with a breathing system. The manometer has a housing with a first chamber and a second chamber. The first chamber is for communication with a breathing gas for respiration of a patient, and the second chamber is cylindrical and graduated with non-linear numerical pressure measurements. The second chamber has a vent at the top which is in communication with ambient air.

The manometer also has a moving member inside the housing. The moving member has a frusto-conical peripheral wall with diameters smaller than the internal diameter of the second chamber. The largest diameter of the moving member faces towards the second chamber. A pointer means is placed adjacent to the largest diameter and is arranged to be visible through the housing as the moving member moves longitudinally within said housing.

A flexible, rolling diaphragm seals the first chamber from the second chamber. The diaphragm has a first edge sealingly attached between the first chamber and the second chamber of the housing and a second edge sealingly attached to the moving member within the housing, thereby forming a seal between the first chamber and the second chamber. The flexible, rolling diaphragm folds upon itself such that two layers of the flexible, rolling diaphragm are between the frusto-conical wall of the moving member and an internal wall of the second chamber.

A port is provided in the first chamber to allow communication with the breathing gas, and a spring is provided in the second chamber. The spring resists the movement of the moving member caused by positive pressure of the breathing gas in the first chamber. The non-linear numerical pressure measurements on the second chamber are calibrated to the spring and the effective diameter of the rolling diaphragm to provide a read out for the pressures of the breathing gas in the first chamber. The read out for the pressure corresponds to the position of the pointer means of the moving member relative to the non-linear numerical pressure graduations.

BRIEF DESCRIPTION OF THE DRAWINGS

FIG. 2 illustrates a sectional view of the manometer in the resting position.

FIG. 3 illustrates a sectional view of the manometer in an intermediate position when pressure is applied to the connector.

DETAILED DESCRIPTION OF THE INVENTION

Figure 1:
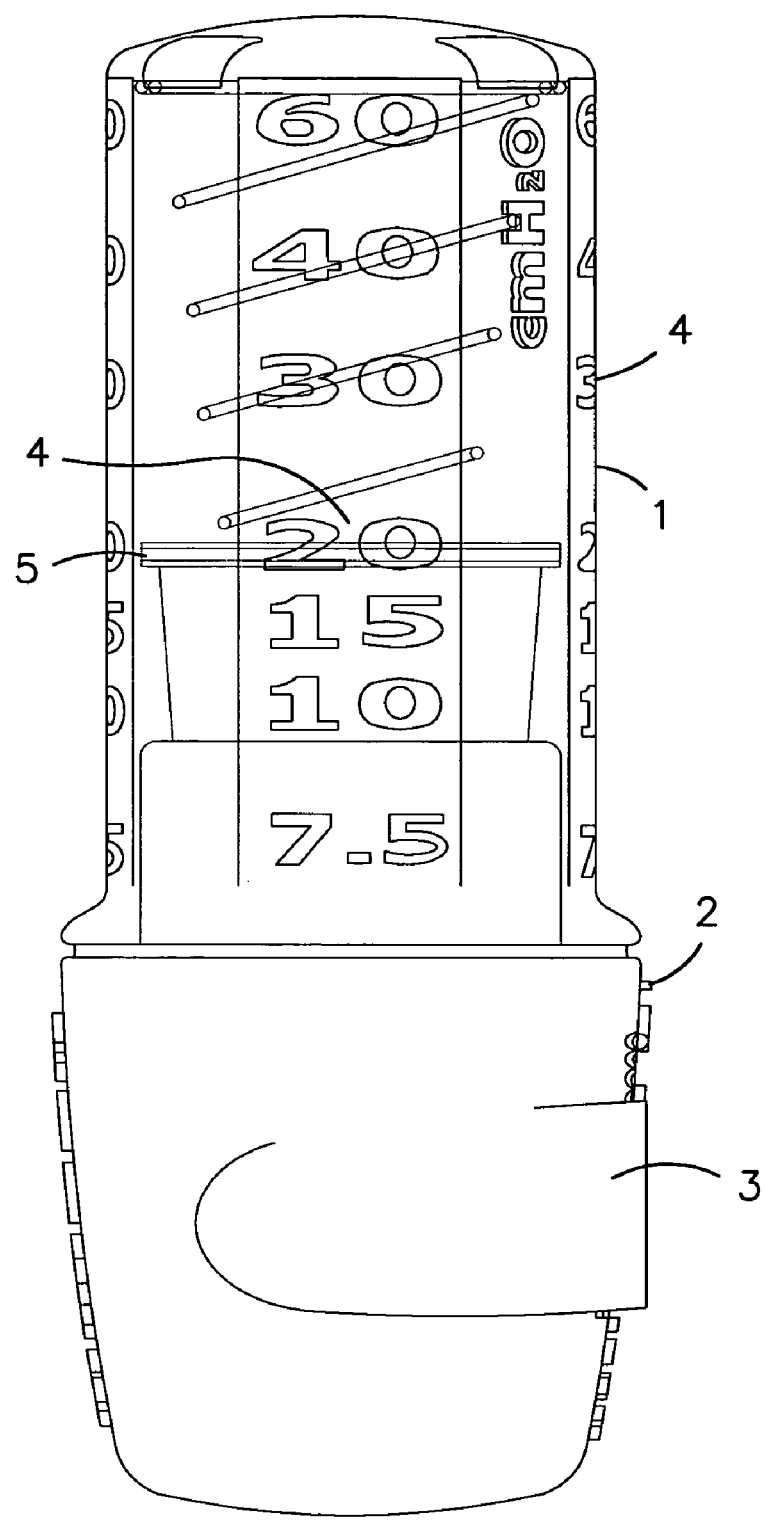
FIG. 1 illustrates a perspective view of the manometer of the invention.

The invention is a disposable manometer for use in a breathing system for monitoring a patient during positive pressure ventilation. The invention is a disposable manometer with a rolling diaphragm sealing mechanism that minimizes leakage in the manometer. The invention combines the rolling diaphragm with a conical frustum moving member to permit near frictionless movement of the moving member. These improvements allow the disposable manometer of the invention to provide accurate readings.

The preferred embodiment of the invention includes a housing within which there is a first or "upper" part and a second or "lower" part sealed from the upper part by an outer circumference of a diaphragm. The housing is preferably cylindrical and contains a moving member to which the inner circumference of the diaphragm is sealed. A calibrated tension means is also provided to resist movement of the moving member in the upper part of the housing caused by the positive pressure of the breathing gas in the lower part of the housing.

The first or upper part of the housing is desirably transparent, or has one or more transparent slots, and is graduated with pressure measurements. The pressure measurements are desirably calibrated in centimeters of water. There can be one set of measurements on the upper part of the cylindrical housing, or there can be several sets to facilitate easier viewing of the correct pressure measured by the manometer from different angles. The top end of the upper part of the housing desirably has vent openings to ensure atmospheric pressure above the moving member and the diaphragm. Desirably, the internal top end of the upper part of the housing is flat.

The calibrated tension means is positioned in the upper part of the housing and is desirably a conical spring. The spring rests on one end against the upper part of the cylindrical housing and on its opposite end against the moving member. The larger diameter end of the spring is compressed against the inner top end of the upper part of the cylindrical housing.

The lower part of the housing is sealed from the upper part by a flexible diaphragm. The lower part of the cylindrical housing is airtight. The connection from the breathing system connects to the lower part of the cylindrical housing.

The flexible diaphragm has an outer circumference and an inner circumference. The outer circumference of the diaphragm forms a seal between the upper part and the lower part of the cylindrical housing. The inner circumference of the diaphragm seals against the conical wall of the moving member. The flexible diaphragm is preferably designed to roll, causing it to fold and unfold on itself, providing near frictionless rising and lowering of the moving member.

The diaphragm is made from a material having a high resiliency. Many polymer materials can provide suitable resiliency for use in fabricating a diaphragm. An example of desirable materials for this purpose includes silicone rubber or other synthetic rubber.

The moving member is desirably a conical frustum with a top end and a bottom end. The top end of the moving member rests against the tension means positioned in the upper part of the housing. The diaphragm is attached near the bottom end of the moving member. The bottom end of the moving member rests in the airtight lower part of the housing when the manometer is not in use.

A connector leads from the lower part of the housing and connects to a breathing system. The connector is desirably a flexible socket made from a non-permeable material.

FIG. 1 shows a side view of a preferred embodiment of the present invention. The manometer housing comprises a transparent, cylindrical upper part 1 attached to an airtight lower part 2 having a connector 3 for attachment to a breathing system monitoring port. The upper transparent housing is graduated with numbers 4 expressing pressure in centimeters of water, when the flange 5 of the mowing member 8 is coinciding with the numbers. The column of pressure measurements is preferably placed in more than one location on the periphery of the transparent housing to allow easy reading from all sides of the manometer.

FIG. 2 shows a sectional view of the manometer in the resting position. The moving member 8 has the shape of a conical frustum and is resting against the conical spring 10 at one end. A rolling diaphragm seal 6 is sealingly attached at one edge near the other end of the moving member 8 by means of a reinforcement 9 resting in a groove on the conical surface. The thin walled rolling diaphragm 6 is made from elastomeric material, e.g., a synthetic rubber, and fits around the conical outer surface of the moving body when folded into itself. The fold fills out the circumferential gap between the moving member and the inside surface of the transparent upper part of the housing, and the other edge of the diaphragm 7 is sealingly attached between the upper and the lower housing parts. The rolling diaphragm 6 thereby seals the cavity of the housing below the moving member from the transparent housing above the moving member and in addition forms a seal between the two housing parts. The rolling diaphragm is made from a material with high resiliency, such as silicone rubber or other synthetic rubber materials. The elastic folding of the rolling diaphragm seal causes the moving member to move without friction. The conical spring 10 rests against a flat surface 12 at the top end of the transparent housing and vent openings 11 are provided to ensure atmospheric pressure above the moving member and the rolling diaphragm.

FIG. 3 shows a sectional view of the manometer in an intermediate position when pressure is applied to the connector 3. The fold of the rolling diaphragm has traveled only half the distance as compared to the upper flange 5 of the moving member 8, and the folding radius has increased as a result of the increased gap between the housing wall and the conical surface of the moving member. The effective surface area will thereby decrease since the diameter of the crest of the fold on the rolling diaphragm will decrease as the moving member moves up. This in turn will cause the moving member gradually to travel less per unit increase in pressure as it moves upwards, thereby causing the manometer to have a non-linear pressure versus movement characteristic. In addition, the non-linear characteristic may be increased further by help of the conical spring 10 as shown in FIG. 3. By dimensioning the spring so that the windings 13 will gradually be pressed flat against surface 12 on top of the housing, the spring stiffness will increase as the moving member moves upwards. The non-linear characteristic has the desirable effect that the relevant range of ventilation pressure can be measured with a manometer according to this invention without any need for excessive length of the instrument. The accuracy of reading may be made almost a constant percentage of the actual reading over the full range of pressures as indicated by the numbers in FIG. 1.

Figure 4:
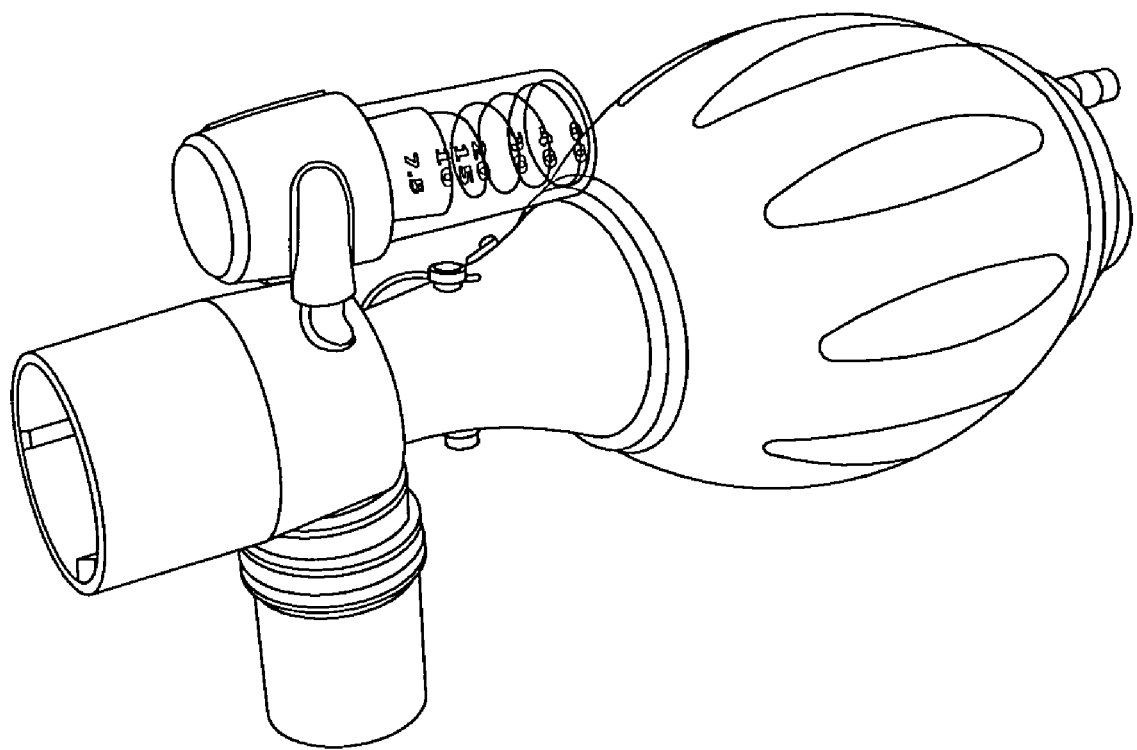
FIG. 4 illustrates a preferred embodiment of the manometer attached to a neonatal-size, manually operated resuscitator.

FIG. 4 shows a preferred embodiment of the manometer attached to a neonatal size manually operated resuscitator.

In view of the many changes and modifications that can be made without departing from principles underlying the invention, reference should be made to the appended claims for an understanding of the scope of the protection to be afforded the invention.

What is claimed is:

1. A disposable manometer for use with a breathing system comprising:
   a housing having a first chamber and a second chamber, said first chamber is for communication with a breathing gas for respiration of a patient and said second chamber is cylindrical and graduated with non-linear numerical pressure measurements, said second chamber has a vent, said vent is in communication with ambient air;
   a moving member, said moving member has a frusto-conical peripheral wall with diameters smaller than the internal diameter of said second chamber and the largest diameter of the moving member facing towards the second chamber, said moving member has pointer means placed adjacent to its largest diameter and arranged to be visible through the housing, said moving member moves longitudinally within said housing;
   a flexible, rolling diaphragm having a first edge sealingly attached between said first chamber and said second chamber of said housing and a second edge sealingly attached to said moving member within said housing thereby forming a seal between said first chamber and said second chamber of said housing, said flexible, rolling diaphragm folds upon itself such that two layers of said flexible, rolling diaphragm are between said frusto-conical wall of said moving member and an internal wall of said second chamber;
   a port to said first chamber, said port is in communication with said breathing gas; and
   a spring in said second chamber, said spring is resisting movement of said moving member caused by positive pressure of said breathing gas in said first chamber; said non-linear numerical pressure measurements are calibrated to said spring and the effective diameter of said rolling diaphragm to provide read out for pressures of said breathing gas in said first chamber corresponding to the positions of said pointer means of said moving member relative to said non-linear numerical pressure graduations.

2. The manometer of claim 1 wherein said rolling diaphragm is made from elastomeric materials comprising silicone rubber or synthetic rubber.

3. The manometer of claim 2 wherein the folding radius of said rolling diaphragm increases, and thereby causing the effective surface area of said rolling diaphragm to decrease, as said moving member moves longitudinally within said housing when said manometer is in communication with said breathing gas.

4. The manometer of claim 3 wherein the relationship of said movement of said moving member and the applied pressure from said breathing gas is non-linear.

5. The manometer of claim 1 wherein said manometer further comprises a connector to connect said port of said manometer to a breathing system.

6. The manometer of claim 5 wherein said connector is placed substantially perpendicular to the length axis of the manometer housing to allow orientation of said manometer in different directions.

7. The manometer of claim 1 wherein said cylindrical upper part is graduated with numerical pressure measurements in centimeters of water at several locations on its periphery.

8. The manometer of claim 1 wherein said spring is positioned between said the top end of said largest diameter of said moving member and the inner surface of the top end of said second chamber.

9. The manometer of claim 8 wherein said spring is conical with the larger diameter end positioned at said inner surface of said top end of said second chamber and the smaller diameter end positioned at said top end of said largest diameter of said moving member.

10. The manometer of claim 9 wherein the windings of said conical spring are gradually compressed flat against said inner surface of said top end of said second chamber and wherein the stiffness of said spring increases in a non-linear manner as said spring is compressed.

11. A disposable manometer for use with a breathing system comprising:
    a cylindrical housing having a transparent upper chamber with a vent in communication with ambient air and graduated with non-linear numerical pressure measurements in centimeters of water at several locations on its periphery, and an airtight lower chamber in communication with a breathing gas for respiration of a patient;
    a moving member, said moving member has a frusto-conical peripheral wall with diameters smaller than the internal diameter of said second chamber and the largest diameter of the moving member facing towards the second chamber, said moving member has pointer means placed adjacent to its largest diameter and arranged to be visible through the housing, said moving member moves longitudinally within said housing;
    a synthetic rubber, rolling diaphragm having a first edge sealingly attached between said first chamber and said second chamber of said housing and a second edge sealingly attached to said moving member within said housing thereby forming a seal between said first chamber and said second chamber of said housing, said flexible, rolling diaphragm folds upon itself such that two layers of said flexible, rolling diaphragm are between said frusto-conical wall of said moving member and an internal wall of said second chamber and wherein the folding radius of said rolling diaphragm increases as said moving member moves longitudinally within said housing when said manometer is in communication with said breathing gas;
    a port to said first chamber, said port is connected to a breathing system through a connector placed substantially perpendicular to the length axis of said manometer housing to allow orientation of said manometer in different directions; and a conical spring in said second chamber, said spring is resisting movement of said moving member caused by positive pressure of said breathing gas in said first chamber; said non-linear numerical pressure measurements are calibrated to said conical spring and the effective diameter of said rolling diaphragm to provide read-out for pressures of said breathing gas in said first chamber corresponding to the positions of said pointer means of said moving member relative to said non-linear numerical pressure graduations.

* * * * *